(12) United States Patent
Meng et al.

(10) Patent No.: US 9,155,765 B2
(45) Date of Patent: Oct. 13, 2015

(54) ESTABLISHMENT OF PATIENT- OR PERSON-SPECIFIC CARDIAC MYOCYTE CELL LINES FROM HUMAN INDUCED PLURIPOTENT STEM CELLS (IPSCS)

(75) Inventors: Xingli Meng, Allen, TX (US); Raphael Schiffmann, Rockwall, TX (US); Jinsong Shen, Allen, TX (US)

(73) Assignee: Baylor Research Institute, Dallas, TX (US)

( * ) Notice: Subject to any disclaimer, the term of this patent is extended or adjusted under 35 U.S.C. 154(b) by 0 days.

(21) Appl. No.: 13/535,964

(22) Filed: Jun. 28, 2012

(65) Prior Publication Data

US 2013/0011371 A1    Jan. 10, 2013

Related U.S. Application Data

(60) Provisional application No. 61/504,637, filed on Jul. 5, 2011.

(51) Int. Cl.

| | | |
|---|---|---|
| *A61P 9/10* | (2006.01) | |
| *A61P 7/04* | (2006.01) | |
| *C12Q 1/68* | (2006.01) | |
| *A61P 25/00* | (2006.01) | |
| *C12N 5/077* | (2010.01) | |
| *C12Q 1/02* | (2006.01) | |
| *G01N 33/566* | (2006.01) | |
| *A61K 35/34* | (2015.01) | |
| *C12N 15/87* | (2006.01) | |
| *A61P 9/00* | (2006.01) | |
| *G01N 33/50* | (2006.01) | |
| *G01N 33/68* | (2006.01) | |

(52) U.S. Cl.
CPC .............. *A61K 35/34* (2013.01); *C12N 5/0657* (2013.01); *G01N 33/5044* (2013.01); *G01N 33/6893* (2013.01); *C12N 2506/45* (2013.01); *G01N 2800/32* (2013.01)

(58) Field of Classification Search
None
See application file for complete search history.

(56) References Cited

U.S. PATENT DOCUMENTS

| 7,452,718 | B2 | 11/2008 | Gold et al. ................ 435/377 |
|---|---|---|---|
| 7,611,852 | B2 | 11/2009 | Thomson et al. ............ 435/7.21 |
| 8,058,065 | B2 * | 11/2011 | Yamanaka et al. ............ 435/377 |
| 2005/0037489 | A1 | 2/2005 | Gepstein et al. ............. 435/366 |
| 2005/0054092 | A1 | 3/2005 | Xu et al. .................... 435/366 |
| 2009/0017465 | A1 | 1/2009 | Xu .............................. 435/6.17 |
| 2011/0097799 | A1 | 4/2011 | Stankewicz et al. .......... 435/377 |

FOREIGN PATENT DOCUMENTS

WO    WO 2004/011603    2/2014

OTHER PUBLICATIONS

Meng, Xing-Li; et al; "Induced pluripotent stem cells derived from mouse models of lysosomal storage disorders" Proceedings of the National Academy of Sciences, 107, 7886-7891 [and supplemental pp. S1-S2], 2010.*
Laflamme, Michael; et al "Cardiomyocytes derived from human embryonic stem cells in pro-survival factors enhance function of infarcted rat hearts" Nature Biotechnology, 25, 1015-1024, 2007.*
Fairchild, Paul J; "The challenge of immunogenicity in the quest for induced pluripotency" Nature Reviews Immunology, 10, 868-875, 2010.*
Ahmed, R. P. H. et al., "Reprogramming of skeletal myoblasts for induction of pluripotency for tumor-free cardiomyogenesis in the infarcted heart", Circulation Research, published online May 12, 2011, vol. 109, pp. 60-70.
Germain, D. P., "Fabry disease", Orphanet Journal of Rare Diseases, 2010, vol. 5, Article No. 30, pp. 1-49.
International Search Report, for International Patent Application No. PCT/2012/044582, dated Aug. 20, 2012.
Kehat I, et al. (2001) Human embryonic stem cells can differentiate into myocytes with structural and functional properties of cardiomyocytes. J Clin Invest 108(3):407-414.
Laflamme MA, et al. (2007) Cardiomyocytes derived from human embryonic stem cells in pro-survival factors enhance function of infarcted rat hearts. Nat Biotechnol 25(9):1015-1024.
Lloyd-Jones D, et al. (2009) Heart disease and stroke statistics—2009 update: a report from the American Heart Association Statistics Committee and Stroke Statistics Subcommittee. Circulation. 119(3):e21-181.
Meng, X.-L. et al., "Induced pluripotent stem cells derived from mouse models of lysosomal storage disorders", Proceedings of the National Academy of Sciences of the United States of America, Apr. 2010, vol. 107, No. 17, pp. 7886-7891.
Mummery C, et al. (2003) Differentiation of human embryonic stem cells to cardiomyocytes: role of coculture with visceral endoderm-like cells. Circulation 107(21):2733-2740.
Paige SL, et al. (2010) Endogenous Wnt/beta-catenin signaling is required for cardiac differentiation in human embryonic stem cells. PLoS One 5(6):e11134.
Taylor DA, Zenovich AG. (2008) Cardiovascular cell therapy and endogenous repair. Diabetes Obes Metab. 10 Suppl 4:5-15.

(Continued)

*Primary Examiner* — Blaine Lankford
*Assistant Examiner* — David Berke-Schlessel
(74) *Attorney, Agent, or Firm* — Norton Rose Fulbright US LLP

(57) ABSTRACT

A composition and method for generating patient- or person-specific proliferative and substantially pure cardiac myocyte cell lines from pluripotent stem cells (iPSCs) is described herein. The patient-specific cardiac myocyte cell lines of the present invention find applications in research, drug screening and autologous cell-based therapy. The method of the present invention is simple and reproducible and generates cardiac myocyte cells having high purities and proliferating capacities.

18 Claims, 8 Drawing Sheets

(56) References Cited

OTHER PUBLICATIONS

Xu C, et al. (2002) Characterization and enrichment of cardiomyocytes derived from human embryonic stem cells. Circ Res 91(6):501-508.

Yang L, et al. (2008) Human cardiovascular progenitor cells develop from a KDR+ embryonic-stem-cell-derived population. Nature 453(7194):524-528.

Yazawa M, et al. (2011) Using induced pluripotent stem cells to investigate cardiac phenotypes in Timothy syndrome. Nature 471(7337):230-234.

Zhang J, et al. (2009) Cardiac bodies: a novel culture method for enrichment of cardiomyocytes derived from human embryonic stem cells. Functional cardiomyocytes derived from human induced pluripotent stem cells. Circ Res 104(4):e30-41.

* cited by examiner

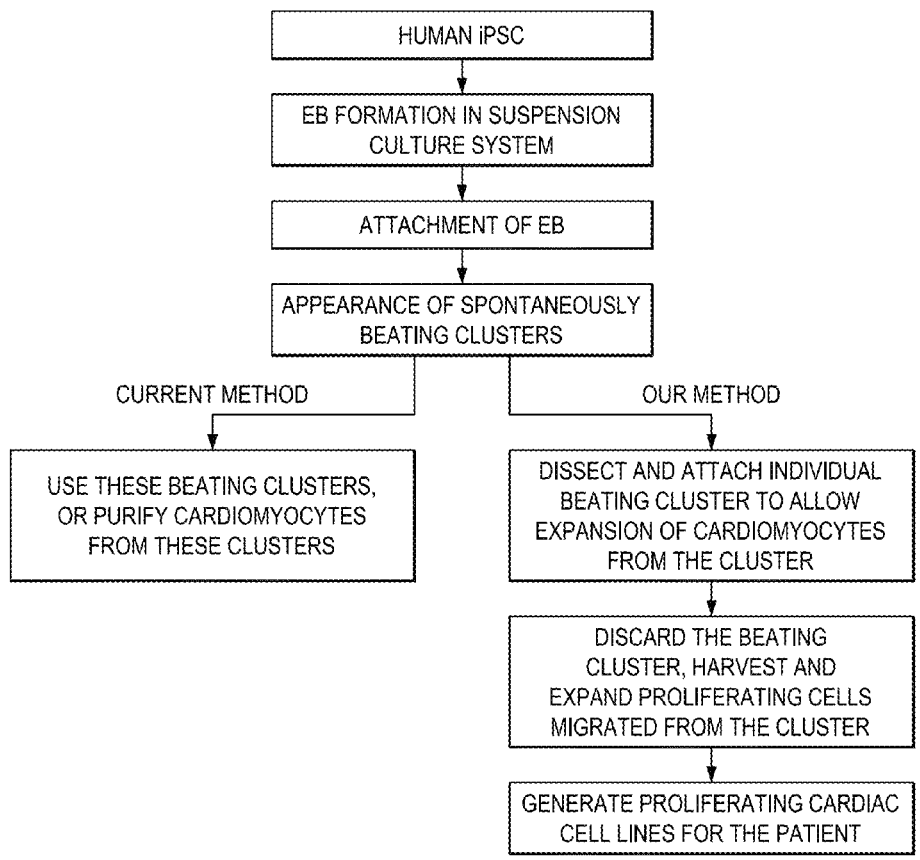

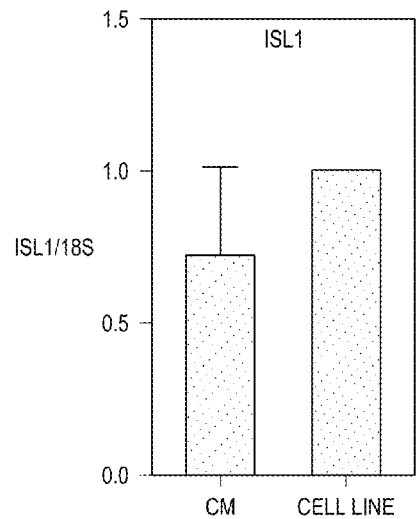
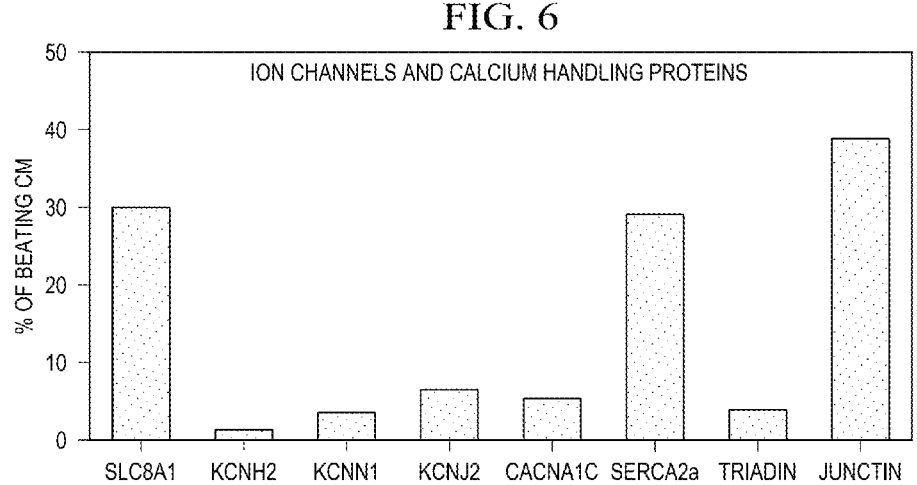

ESTABLISHMENT OF PATIENT- OR PERSON-SPECIFIC CARDIAC MYOCYTE CELL LINES FROM HUMAN INDUCED PLURIPOTENT STEM CELLS (IPSCS)

CROSS-REFERENCE TO RELATED APPLICATIONS

This application claims priority to U.S. Provisional Application Ser. No. 61/504,637, filed Jul. 5, 2011 the entire contents of which are incorporated herein by reference.

TECHNICAL FIELD OF THE INVENTION

The present invention relates in general to techniques for differentiating and proliferating pluripotent stem cells, and more particularly, to novel technology for generating patient-specific cardiac myocyte cell lines from human fibroblast-derived pluripotent stem cells.

STATEMENT OF FEDERALLY FUNDED RESEARCH

None.

REFERENCE TO A SEQUENCE LISTING

None.

BACKGROUND OF THE INVENTION

Without limiting the scope of the invention, its background is described in connection with generation of cardiac cell lines and tissues for research, drug screening and autologous cell-based therapy by in vitro culturing of differentiable cells and other related methods.

One such method is taught in PCT Patent Application No. PCT/US2011/056329, filed by Singla, et al., entitled, Cardiac Induced Pluripotent Stem Cells And Methods Of Use In Repair And Regeneration Of Myocardium. Briefly, this application is said to disclose iPS cells from cardiac or ventricular specific cell types that are generated having the potential to repair and regenerate infarcted myocardium. The cells were transduced with four sternness factors and reprogrammed them into iPS cells. These cardiac iPS cells were able to differentiate into beating cardiac myocytes, formed cardiac-specific structures, and positively stained for cardiac specific proteins. Transplanted cells also significantly inhibited apoptosis and fibrosis and improved cardiac function.

Another application is U.S. Patent Application No. 2011/097799, filed by Stankewicz, et al., entitled, Cardiomyocyte Production. Briefly, methods and composition for the production of cardiomyocytes from differentiation of pluripotent stem cells are disclosed. For example, in certain aspects methods including differentiating pluripotent stem cells in a large volume of suspension culture in the presence of Rho-associated (ROCK) inhibitors are described. Also, methods for differentiation of stem cells into cardiomyocytes that overcome variability between different stem cell clones and different batch of culture medium are said to be provided.

Another such technique for generating cells predominantly displaying at least one characteristic associated with a cardiac phenotype is disclosed in U.S. Patent Application Publication No. 2005/037489 (Gepstein et al. 2005) (hereinafter Gepstein). The Gepstein invention comprises the steps of (a) partially dispersing a confluent cultured population of human stem cells, thereby generating a cell population including cell aggregates; (b) subjecting said cell aggregates to culturing conditions suitable for generating embryoid bodies; (c) subjecting said embryoid bodies to culturing conditions suitable for inducing cardiac lineage differentiation in at least a portion of the cells of said embryoid bodies, said culturing conditions suitable for inducing cardiac lineage differentiation including adherence of said embryoid bodies to a surface, and culture, medium supplemented with serum, thereby generating cells predominantly displaying at least one characteristic associated with a cardiac phenotype.

U.S. Patent Application Publication No. 2005/0054092 (Xu and Gold, 2005) provides a method of obtaining populations of human cells of the cardiomyocyte lineage. The cells are said to be obtained by causing cultures of pluripotent stem cells to differentiate in vitro, and then harvesting cells with certain phenotypic features. Differentiated cells bear cell surface and morphologic markers characteristic of cardiomyocytes, and a proportion of them undergo spontaneous periodic contraction. Highly enriched populations of cardiomyocytes and their replicating precursors can be obtained, and are suitable for use in a variety of applications, such as drug screening and therapy for cardiac disease.

A procedure for generating cardiomyocyte lineage cells from embryonic stem cells for use in regenerative medicine is described in U.S. Pat. No. 7,452,718 issued to (Gold et al. 2008) (hereinafter the '718 patent). The '718 patent describes a method that does not require differentiating by way of embryoid body formation or in serum. Instead, the stem cells are plated onto a solid substrate, and differentiated in the presence of select factors and morphogens. After enrichment for cells with the appropriate phenotype, the cells are allowed to cluster into cardiac Bodies™, which are remarkably homogeneous and suitable for the treatment of heart disease.

U.S. Patent Application Publication No. 2009/0017465 (Xu, 2009) provides populations human cells of the cardiomyocyte lineage. The cells are obtained by causing cultures of pluripotent stem cells to differentiate in vitro, and then harvesting cells with certain phenotypic features. Differentiated cells bear cell surface and morphologic markers characteristic of cardiomyocytes, and a proportion of them undergo spontaneous periodic contraction. Highly enriched populations of cardiomyocytes and their replicating precursors can be obtained, suitable for use in a variety of applications, such as drug screening and therapy for cardiac disease.

Finally, U.S. Pat. No. 7,611,852 issued to (Thomson et al., 2009) discloses human embryonic stem cells form embryoid bodies in culture, which contain differentiated human cells. Some of the human cells in embryoid bodies differentiate into cardiomyocytes. Here the biological and electrical characteristics of those cardiomyocytes are described with reference to the use of cardiomyocytes derived from human embryonic stem cells in drug screening protocols for mechanisms of cardiac toxicity.

SUMMARY OF THE INVENTION

The present invention includes compositions and methods for generating patient-specific cardiac myocyte cell lines from, e.g., human fibroblast-derived pluripotent stem cells to be used as a highly proliferative and pure source for a cardiovascular disease study and cell-based therapy. The present invention allows the generation of patient-specific cardiac myocyte cell lines that are proliferative and thus can provide a large number of cells and in a highly pure population. This makes them highly desirable for a variety of research and autologous cell-based therapy for individual patients.

In one embodiment the instant invention provides a method of generating a cell line or a cellular composition from one or more induced pluripotent stem cells (iPSCs) comprising the steps of: (a) obtaining the one or more iPSCs; (b) initiating differentiation of the one or more iPSCs; (c) separating one or more cells or a cellular cluster exhibiting spontaneous beating; (d) performing a first culturing on the differentiated cells or the cellular cluster for a specified period of time; (e) separating one or more cells or a cellular cluster exhibiting spontaneous beating from the first culture; (f) performing a second culturing on the differentiated cells or the cellular cluster from the first culture for a specified period of time; (g) removing one or more cells or a cellular cluster exhibiting spontaneous beating from the second culture leaving one or more differentiated cells in the second culture; (h) harvesting the one or more differentiated cells that remain in the second culture; and (i) expanding the harvested differentiated cells from the second culture to obtain the cell line or the cellular composition.

In another aspect of the present invention the method comprises the step of repeating one or more steps in steps (c) through (h). In one feature of the present invention the step of obtaining the one or more iPSCs comprises the steps of: (i) providing a primary culture comprising one or more non-pluripotent cells obtained from a mammalian subject and (ii) transfecting one or more transcription factors or stem-cell associated genes into the one or more non-pluripotent cells, wherein the transfection results in the formation of the iPSCs from the non-pluripotent cells. In another aspect the non-pluripotent cells comprises fibroblasts, blastocytes, keratocytes, aminocytes, gastric cells, neural stem cells, or any combination thereof. In yet another aspect the one or more transcription factors are selected from the group consisting of Sox2, Oct3/4, Klf4, c-Myc, Lin28, Nanog, or any combination thereof. In one aspect, the mammalian subject is a human subject, wherein the subject is at least one of a healthy subject, a subject suffering from one or more metabolic disorders, cardiovascular diseases, cardiac dysfunction, myocardial infarction, myocardial ischemia, myocardial reperfusion, subendocardial ischemia, Takayasu's arteritis, atrial fibrillation, hemorrhagic strokes, ischemia/reperfusion, reperfusion injury, congenital heart disease, or cardiac surgery.

In specific aspects related to the method, the metabolic disorder is Fabry's disease and the cell line comprises a cardiac cell line. In another aspect, the cell line or the cellular composition comprises cardiomyocytes. In yet another aspect, the step of initiating differentiation of the one or more iPSCs comprises formation of one or more embryoid bodies, or by exposing iPSCs to factors such as BMP4 or activin A. In one aspect, the separation of one or more cells or a cellular cluster exhibiting spontaneous beating is by one or more mechanical methods. In another aspect the separated cells or cellular cluster exhibiting differentiation comprises one or more beating cells. In yet another aspect, the harvesting of the one or more differentiated cells is done by trypsinization or by mechanical dissociation using a cell scrapper followed by repeated pipetting. In a specific feature, the cell line or the cellular composition obtained by the method described hereinabove is >90% pure. Finally, the cell line or cellular composition obtained by the method of the present invention is adapted for use in cellular/tissue transplantation, drug activity and toxicity screening studies, in vitro mechanistic disease models, cell-based therapies, optimizing a therapeutic regimen, or any combinations thereof.

Another embodiment of the present invention provides a method of generating a cardiac cell line or a cellular composition of cardiomyocytes from one or more induced pluripotent stem cells (iPSCs) comprising the steps of: (i) obtaining the one or more iPSCs; (ii) initiating differentiation of the one or more iPSCs; (iii) separating one or more cells, or a cellular cluster exhibiting differentiation, wherein the one or more cells, or the cellular clusters exhibiting differentiation comprise beating cardiac myocytes; (iv) performing a first culturing on the differentiated cardiac myocytes cells or the cellular cluster for a specified period of time; (v) separating the one or more cardiac myocyte cells, or a cellular cluster exhibiting spontaneous beating from the first culture; (vi) performing a second culturing on the separated and differentiated cardiac myocyte cells or the cellular cluster from the first culture for a specified period of time; (vii) removing one or more cardiac myocyte cells, or a cellular cluster exhibiting spontaneous beating from the second culture leaving behind one or more differentiated cardiac myocyte cells in the second culture; (viii) harvesting the one or more cells differentiated cardiac myocyte cells left behind in the second culture; and (ix) expanding the harvested differentiated cardiac myocyte cells from the second culture to obtain the cardiac cell line or a cellular composition of cardiomyocytes. The method as described hereinabove further comprises the steps of repeating one or more steps in steps (iii) through (viii). In one aspect of the method described above, the step of obtaining the one or more iPSCs comprises the steps of: providing a primary culture comprising one or more skin fibroblast cells obtained from a mammalian subject and transfecting one or more transcription factors selected from the group consisting of Sox2, Oct3/4, Klf4, c-Myc, or any combination thereof into the one or more skin-fibroblast cells, wherein the transfection results in the formation of the iPSCs from the skin-fibroblast cells. In one aspect, the mammalian subject is a human subject, wherein the subject is at least one of a healthy subject, a subject suffering from one or more metabolic disorders, cardiovascular diseases, cardiac dysfunction, myocardial infarction, myocardial ischemia, myocardial reperfusion, subendocardial ischemia, Takayasu's arteritis, atrial fibrillation, hemorrhagic strokes, ischemia/reperfusion, reperfusion injury, congenital heart disease, or cardiac surgery. In a specific aspect, the metabolic disorder is Fabry's disease. In yet another aspect, the cardiac cell line or the cardiomyocyte cells have a purity of about 100%. In a related aspect the cardiac cell line or the cardiomyocyte cell composition is adapted for use in cellular/tissue transplantation, drug screening studies, in vitro mechanistic disease models, cell-based therapies, optimizing a therapeutic regimen, or any combination thereof. The cardiac cell line or the cardiomyocyte cell composition obtained by the method herein exhibits myotube formation, shows continuous proliferation for up to at least 12 passages, and expresses sarcomeric α-actinin, transcription factor GATA-4, sarcomeric myosin heavy chain (MF20), cardiac troponin T, human NKx2.5 and myosin light chain 2v or any combination thereof.

In yet another embodiment, the instant invention provides an in vitro system or model for disease mechanistic studies, for diagnosing one or more cardiovascular diseases, cardiac complications of one or more metabolic disorders, screening activity, toxicity, or both of one or more cardiovascular drugs, optimizing a cardiac therapy regimen, or any combination thereof comprising: providing one or more cardiac myocyte cell lines or a composition comprising one or more cardiomyocyte cells, combining a candidate drug with an in vitro system comprising a cardiac myocyte cell line, or a composition comprising a population of one or more cardiomyocyte cells, wherein at least a portion of the cell line or the cardiomyocyte cells is capable of proliferation, myotube formation, cardiac marker expression, or any combination thereof, monitoring for changes in an activity, an expression, a morphology, or any combination thereof in the cardiac myocyte cell line, or the cardiomyocyte cells that result from being combined with the candidate drug, and correlating the change in the activity, the expression, the morphology in the cardiac myocyte cell line or the cardiomyocyte cells with the activity, the effectiveness, or both of the candidate drugs.

The cardiac myocyte cell line, or a composition comprising one or more cardiomyocyte cells used hereinabove is generated using a method comprising the steps of: (a) obtaining the one or more iPSCs; (b) initiating differentiation of the one or more iPSCs; (c) separating one or more cells or a cellular cluster exhibiting differentiation, wherein the one or more cells or the cellular clusters exhibiting differentiation comprise beating cardiac myocytes; (d) performing a first culturing on the differentiated cardiac myocytes cells or the cellular cluster for a specified period of time; (e) separating the one or more cardiac myocyte cells or a cellular cluster exhibiting spontaneous beating from the first culture; (f) performing a second culturing on the separated and differentiated cardiac myocyte cells or the cellular cluster from the first culture for a specified period of time; (g) removing one or more cardiac myocyte cells or a cellular cluster exhibiting spontaneous beating from the second culture leaving one or more differentiated cardiac myocyte cells in the second culture; (h) harvesting the one or more cells differentiated cardiac myocyte cells that remain in the second culture; and (i) expanding the harvested differentiated cardiac myocyte cells from the second culture to obtain the cardiac cell line or a cellular composition of cardiomyocytes. The system as described herein, further comprises the steps of repeating one or more steps in steps (c) through (h). In one aspect of the model the step of obtaining the one or more iPSCs comprises the steps of: Providing a primary culture comprising one or more skin fibroblast cells obtained from a mammalian subject and transfecting one or more transcription factors selected from the group consisting of Sox2, Oct3/4, Klf4, c-Myc, or any combination thereof into the one or more skin-fibroblast cells, wherein the transfection results in the formation of the iPSCs from the skin-fibroblast cells. In one aspect, the mammalian subject is a human subject, wherein the subject is at least one of a healthy subject, a subject suffering from one or more metabolic disorders, cardiovascular diseases, cardiac dysfunction, myocardial infarction, myocardial ischemia, myocardial reperfusion, subendocardial ischemia, Takayasu's arteritis, atrial fibrillation, hemorrhagic strokes, ischemia/reperfusion, reperfusion injury, congenital heart disease, or cardiac surgery. In specific aspects, the metabolic disorder is Fabry's disease and the cardiac cell line or the cardiomyocyte cells have a purity of about 100%. The present invention also provides a composition for treating one or more cardiovascular diseases or cardiovascular complications of Fabry's disease in a human or animal subject comprising a cardiac myocyte cell line, or a composition comprising one, or more cardiomyocyte cells, wherein the cardiac myocyte cell line, or composition comprising one, or more cardiomyocyte cells is generated by the method as described previously hereinabove.

In another embodiment, the present invention discloses a method of treating, or optimizing therapy of one or more cardiovascular diseases, or cardiovascular complications of Fabry's disease in a human or animal subject comprising the steps of: Identifying the human or animal subject in need of treatment against the one or more cardiovascular diseases, or cardiovascular complications of Fabry's disease; and transplanting in the human or animal subject a therapeutically effective amount of a composition comprising a cardiac myocyte cell line or a composition comprising one or more cardiomyocyte cells. The cardiac myocyte cell line or composition comprising one or more cardiomyocyte cells as used in the method herein is generated by the method described previously.

The present invention in one embodiment describes a method of evaluating effectiveness, screening activity, toxicity, or both of a candidate drug, or both against one or more cardiovascular diseases or cardiovascular complications of Fabry's disease in a human or animal subject comprising: Providing the candidate drug against the one or more cardiovascular diseases or the cardiovascular complication of Fabry's disease, combining the candidate drug with an in vitro system comprising a cardiac myocyte cell line or a composition comprising a population of one or more cardiomyocyte cells, wherein at least a portion of the cell line or the cardiomyocyte population is capable of proliferation, myotube formation, cardiac marker expression, or any combination thereof, monitoring for changes in an activity, an expression, a morphology, or any combinations thereof of in the cardiac myocyte cell line, or the cardiomyocyte cell population that results from being combined with the candidate drug, and correlating the change in the activity, the expression, the morphology in the cardiac myocyte cell line, or the cardiomyocyte cell population with the activity, the effectiveness, or both of the candidate drugs. In one aspect, the cardiac myocyte cell line or composition comprising one or more cardiomyocyte cells is generated by the method previously described herein.

In another embodiment the present invention relates to an in vitro disease model for detecting one or more cardiovascular diseases, one or more cardiac complications of Fabry's disease, or both comprising a cardiac myocyte cell line or a composition comprising a population of one or more cardiomyocyte cells, wherein at least a portion of the cell line or the cardiomyocyte population is capable of proliferation, myotube formation, cardiac marker expression, or any combination thereof, wherein the cardiac myocyte cell line or the composition comprising the population of one or more cardiomyocyte cells is generated from one or more induced pluripotent stem cells (iPSCs) obtained from a healthy subject, a subject suffering from one or more cardiovascular diseases or metabolic disorders, or both. In one aspect, the cardiac myocyte cell line or composition comprising one or more cardiomyocyte cells obtained from the iPSCs is generated by the method previously described.

In yet another embodiment, the present invention discloses a method for detecting, studying, evaluating risk, or any combination thereof one or more cardiovascular diseases, one or more cardiac complications of Fabry's disease, or both comprising the steps of: (i) providing an in vitro disease model comprising a cardiac myocyte cell line or a composition comprising one or more cardiomyocyte cells, wherein at least a portion of the cell line or the cardiomyocyte cells is capable of proliferation, myotube formation, cardiac marker expression, or any combination thereof, wherein the cardiac myocyte cell line or the composition comprising the cardiomyocyte cells is generated from one or more induced pluripotent stem cells (iPSCs) obtained from a healthy subject, a subject suffering from one or more cardiovascular diseases or metabolic disorders, or both, (ii) monitoring for changes in an activity, an expression, a morphology, or any combinations thereof of in the cardiac myocyte cell line or the cardiomyocyte cells under normal or stressed physiological conditions, upon exposure to one or more drugs or cardioactive agents, or any combinations thereof and (iii) correlating the change in the activity, the expression, the morphology in the cardiac myocyte cell line or the cardiomyocyte cells with either the presence, absence, or the risk for developing one or more cardiovascular diseases, one or more cardiac complications of Fabry's disease, or both. In one aspect the cardiac myocyte cell line or composition comprising one or more cardiomyocyte cells obtained from the iPSCs is generated by the methods described previously herein.

BRIEF DESCRIPTION OF THE DRAWINGS

For a more complete understanding of the features and advantages of the present invention, reference is now made to the detailed description of the invention along with the accompanying figures and in which:

FIG. 1A is a schematic showing differences in the techniques between existing methods and the present invention for generating cardiac myocytes from induced pluripotent stem cells (iPSCs);

FIG. 1B is a comparison of the characteristics of the cardiac myocytes from iPSCs obtained using existing method and the method as described in various embodiments of the present invention;

FIG. 5 shows ISL1 mRNA expression in derived cardiac cell line and beating clusters of cardiomyocytes (CM).

FIG. 6 shows a quantitative mRNA analysis of ion channel subunits and Ca2+ handling proteins in derived cardiac cell line.

DETAILED DESCRIPTION OF THE INVENTION

Figure 2A:
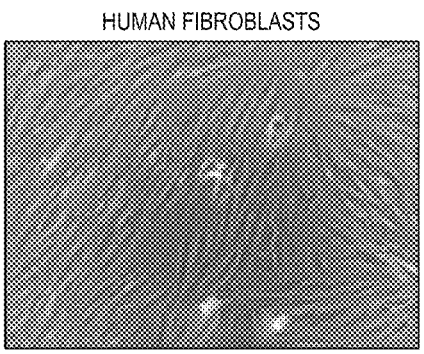
FIGS. 2A-2F show the different steps involved in the generation of cardiac myocytes from patient fibroblasts derived-iPSCs.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an," and "the" are not intended to refer to only a singular entity, but include the general class of which a specific example may be used for illustration. The terminology herein is used to describe specific embodiments of the invention, but their usage does not delimit the invention, except as outlined in the claims.

The term "myocyte" as used herein refers to muscle cells that are characterized by containing myosin. The term "cardiac myocyte" refers to cells containing myosin which are located in, isolated or derived from muscle (myocardium) or conductive tissue of a heart, either isolated or in culture, and capable of initiating a current.

The term "cell line" refers to a clone of immortalized mammalian cells. The terms "cell line" and "established cell line" are used herein in conformance with the definitions published by Federoff in the Tissue Culture Association Manual, Vol. 1, No. 1, pp. 53-57 (1975), which is incorporated herein by reference.

The term "fibroblasts" as described herein refers to main cells in the dermis, which produce connective tissue ingredients such as collagen and the like and form a tissue by binding with these ingredients.

As used herein, the term "pluripotent stem cell" denotes a cell that has the ability to self replicate for indefinite periods and can give rise to many cell types under the right conditions, particularly, the cell types that derived from all three embryonic germ layers—mesoderm, endoderm, and ectoderm.

The term "embryoid bodies" as used herein is a term of art synonymous with "aggregate bodies", referring to aggregates of differentiated and undifferentiated cells that appear when pluripotent stem cells overgrow in monolayer cultures, or are maintained in suspension cultures. "Embryoid bodies" are a mixture of different cell types, typically from several germ layers, distinguishable by morphological criteria and cell markers detectable by immunocytochemistry.

The term "cardiovascular disease," as used herein, is intended to refer to all pathological states leading to a narrowing and/or occlusion of blood vessels throughout the body. In particular, the term "cardiovascular disease" refers to conditions including atherosclerosis, thrombosis and other related pathological states, especially within arteries of the heart and brain. Accordingly, the term "cardiovascular disease" encompasses, without limitation, various types of heart disease, as well as Alzheimer's disease and vascular dimension.

As used herein, the term "metabolic disease," includes a group of identified disorders in which errors of metabolism, imbalances in metabolism, or sub-optimal metabolism occur. The term "metabolic diseases" as used herein also contemplate a disease that can be treated through the modulation of metabolism, although the disease itself may or may not be caused by specific metabolism blockage.

The term "Fabry's disease" as used herein refers to an X-linked inborn error of glycosphingolipid catabolism due to deficient lysosomal α-galactosidase A activity. This defect causes accumulation of globotriaosylceramide (ceramide trihexoside) and related glycosphingolipids in vascular endothelial lysosomes of the heart, kidneys, skin, and other tissues.

The term "polymerase chain reaction" (PCR) refers to the method of K. B. Mullis U.S. Pat. Nos. 4,683,195, 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as DCTP or DATP, into the amplified segment). In addition to genomic DNA, any oligonucleotide sequence can be amplified with the appropriate set of primer molecules. In particular the amplified segments created by the PCR process itself are, themselves, efficient templates for subsequent PCR amplifications.

As used herein, the term "in vivo" refers to being inside the body. The term "in vitro" used as used in the present application is to be understood as indicating an operation carried out in a non-living system.

As used herein, "pharmaceutically acceptable carrier" refers to any material that when combined with an immunoglobulin (Ig) fusion protein of the present invention allows the Ig to retain biological activity and is generally non-reactive with the subject's immune system. Examples include, but are not limited to, standard pharmaceutical carriers such as a phosphate buffered saline solution, water, emulsions such as an oil/water emulsion, and various types of wetting agents. Certain diluents may be used with the present invention, e.g., for aerosol or parenteral administration, that may be phosphate buffered saline or normal (0.85%) saline.

The terms "administration of" or "administering a" compound as used herein refers to providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" as used herein should be understood to indicate the amount of the subject compound that will elicit the biological or medical response of a tissue, system, animal or human that is being sought by the researcher, veterinarian, medical doctor or other clinician.

As used herein, the term "treatment" or "treating" includes any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). Non-limiting examples of diseases that can be treated using the cells of the present invention include cardiac dysfunction, myocardial infarction, myocardial ischemia, myocardial reperfusion, subendocardial ischemia, Takayasu's arteritis, atrial fibrillation, hemorrhagic strokes, ischemia/reperfusion, reperfusion injury, cardiac surgery.

One of the current methods for generating cardiac myocytes is to isolate cardiac myocytes directly from human heart tissue. Cardiac cells generated by this method are commercially available from a few companies including PromoCell (GmbH Heidelberg, Germany) and ScienCell (Carlsbad, Calif.). However, all these cardiac cells are isolated from healthy individuals. The other method used is to differentiate human embryonic stem (ES) cells or induced pluripotent stem cells (iPSCs) into cardiac cells in vitro (1). But current method used for differentiation of cardiomyocytes from pluripotent stem cells in vitro can only provide relative impure cardiac cells with significant contamination of other cell types (about 20%), and with low proliferative capacity, thus, the use of the method in providing commercial cardiac myocytes is limited.

The present invention describes a novel method to generate proliferative and highly pure human cardiac cell lines from induced pluripotent stem cells (iPSCs). Since these cardiac myocyte cell lines are originally generated from skin fibroblasts, the method described herein allows generation of patient- or person-specific cardiac cell lines in vitro. This feature makes the method of the present invention highly useful for basic research and drug screening, cardiac therapy optimization, as well as for treating individual patients, such as by autologous cell transplantation.

The method described herein below is simple and reproducible. Further, it takes only a few months to obtain highly pure cardiac cell lines from skin fibroblasts. Unlike currently available method for obtaining cardiac cells from human iPSCs, cardiac cells generated by the method of the present invention have high proliferating capacity and high purity. These are significant advantages over current methods. Although, the present inventors generated cardiac cells from iPSCs, due to the genetic and phenotypic similarities between iPSCs and ES cells it is possible that cardiac cell lines can be generated from human ES cells or other type of stem cells using this method.

The present inventors have established several cardiac myocyte cell lines from one healthy individual and two different patients with, e.g., Fabry's disease using the method described herein. Cardiac complications are common and major manifestations of Fabry's disease. These Fabry cardiac cell lines (and the cell lines will be generated) are invaluable tools for studying disease mechanism (including relationship between genotype and cardiac phenotypes) and evaluating new treatments for Fabry's heart disease, and thus is of interest researchers in the fields of metabolic disease and cardiovascular diseases.

Cardiovascular heart disease is the leading cause of death, accounts for about 2.5 million deaths each year in the United States (2). The treatment to acute myocardial infarction and risk factors of cardiovascular disease improved the mortality of the patients, but on the other hand increased the number of patients with post-acute myocardial infarction heart failure. Cell-based therapy is of great promise in the treatment of both acute myocardial infarction and chronic heart failure (3). Human cardiac cells are important materials for cell-based therapies as well as other important applications such as drug screening and disease mechanistic studies (4, 5). The purity and proliferative potential of transplantable cardiac cells are two important factors for successful grafting. Currently there is no method for obtaining pure and proliferative cardiac myocyte cell lines from patients. Such cells are very much needed for autologous cell/tissue transplantation and patient-tailored studies.

Human cardiac cells can be obtained and cultured from heart tissue. A few biotechnology companies including PromoCell and ScienCell provide human cardiac cells obtained from normal individuals for research purposes. Theoretically, patient-specific cardiac cells can be obtained from heart biopsy and be cultured by this method. But the invasive procedure and limited amount of heart tissue that can be obtained by biopsy limited the application of this method in clinic.

Pluripotent stem cells including ES cells and induced pluripotent stem cells (iPSCs) are alternative source of human cardiac cells since these stem cells have extraordinary proliferative capacity and can be differentiated into cardiac cell in vitro (6). Because iPSCs can be generated from human skin fibroblasts they have remarkable advantages over human ES cells that have ethical and immune rejection problems. Generating and purification of cardiac cells from human iPSCs is a highly competitive topic at this time point. The current method in obtaining human cardiac myocytes is using the embryoid body (EB)-based differentiation method following percoll gradient separation of the cardiac myocytes from the pool of mixed cell types (1). But the purity of the cells is about 80% and the proliferative ability of the cells is very limited. Transplantation experiments showed the purity and proliferative capacity of the differentiated cardiac myocytes is crucial for a successful transplantation since the higher purity the lower chances of developing teratoma in the graft and a substantial proliferative capacity is required for establishing vascular supply which determines the survival of the graft. Researchers are developing methods in order to increase the purity and number of cardiac myocytes such as cardiac body-enrichment (7), co-culture with visceral endoderm-like cells (8) and lineage-directed cardiac differentiation (9, 10). But none of these is able to obtain highly pure proliferating cardiac myocytes.

The present invention provides a simple method to derive pure or almost pure cardiac myocytes from human iPSCs that can continuously proliferate to more than 12 passages in vitro, e.g., 90%, 95%, 96%, 97%, 98%, 99 or even 100% pure cardiac myocytes from human iPSCs. The method enables establishing patient-specific source of cardiac myocytes for research and therapeutic purpose. The number of passages can be 1, 2, 3, 4, 5, 6, 7, 8, 9, 10, 11, 12 or more. FIG. 1A is a schematic comparison of the method of the present invention and the currently used methods, and FIG. 1B compares the cardiac myocyte cell lines generated by the method of the present invention and the existing technologies.

FIG. 1A is a schematic showing differences in the techniques between existing methods and the present invention for generating cardiac myocytes from induced pluripotent stem cells (iPSCs). Briefly, human iPSC are made in a manner known in the art that includes forming Embryoid Bodies (EBs) in suspension cultures followed by attachment of the EBs. The present invention does not require but can also benefit, in certain examples, from hanging suspension cultures but there are not required. As a consequence of the attachment of the EBs a certain percentage of cells undergo further differentiation into beating clusters. It is at this stage that the present invention differs from the prior art, in which the beating clusters or cardiomyoctes are harvested from these clusters. Instead, the present invention dissects and allows individual beating clusters to attach to allow for the expansion of the cardiomyocytes from the cluster. Next, the beating clusters are discarded, and the cells that proliferate and expand from the beating clusters are allowed to proliferate. These cells are then allowed to further grow and again beating clusters are removed and discarded. The remaining cells can then be harvested and used, are allowed to continue growing or are made into cell lines, thereby allowing for the expansion or large numbers of syngeneic cells that can be reinserted into the patient. FIG. 1B is a comparison of the characteristics of the cardiac myocytes from iPSCs obtained using existing method and the method as described in various embodiments of the present invention, in which the method disclosed herein yields cells with high proliferative capacity, high yield and high purity, in comes cases over 60%, 70%, 80%, 85%, 90% or even 97% of the cells are cardiac iPSCs. It is also possible to pass and expand the cell lines of the present invention numerous times, including 2, 3, 4, 5, 6, 7, 8, 9, 10, 11, 12 or more times.

Figure 2B:
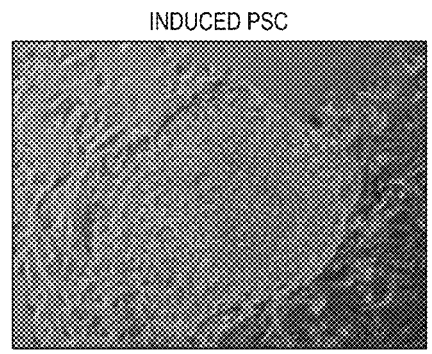
Figure 2C:
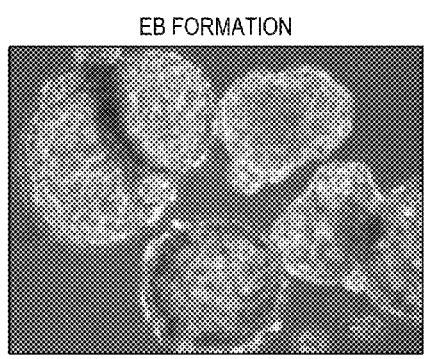
Figure 2D:
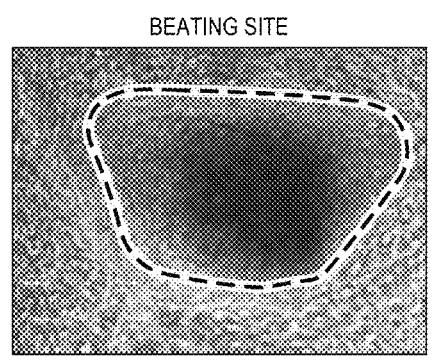
Figure 2E:
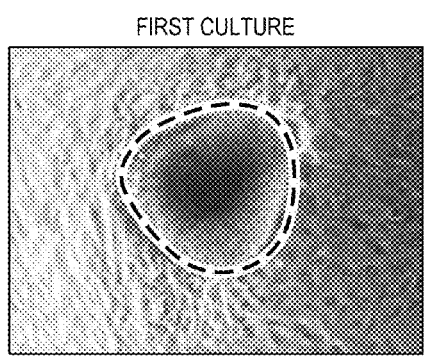
Figure 2F:
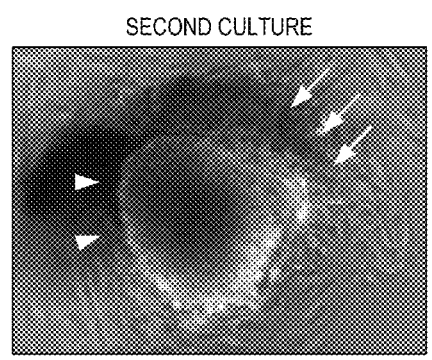

Generation of cardiac cell lines: The inventors generated human iPSCs by transduction of Sox2, Oct3/4, Klf4 and c-Myc into human fibroblasts with/without heart disease (FIGS. 2A and 2B) (e.g., human genes having Accession numbers: NM_003106; NM_001173531; NM_004235; NM_002467, respectively). The present invention discloses a method to generate cardiomyocytes from these human iPSCs. EB formation was initiated from iPSCs in suspension culture and these EBs were attached to obtain beating clusters of cardiac myocytes (FIGS. 2C and 2D). The beating clusters were mechanically dissected and attached to 12-well plate with one cluster per well and cultured for 2 weeks ($1^{st}$ culture, FIG. 2E). In order to increase the purity of cardiac myocyte cell lines the beating clusters in the $1^{st}$ culture were dissected again into new wells (1 cluster/well) to allow for migration of pure cardiac myocytes from the cluster for 2 weeks ($2^{nd}$ culture, FIG. 2F). Then, beating clusters in the $2^{nd}$ culture (FIG. 2F, indicated with arrowheads) were removed and the migrated cells (FIG. 2F, arrows) were harvested by trypsinization. Cells from each cluster were expanded as one cardiac myocyte cell line. Using the present invention it was possible to obtain several cardiac cell lines from one patient/person, which are made spontaneously during the use of the method of the present invention.

Figure 3:
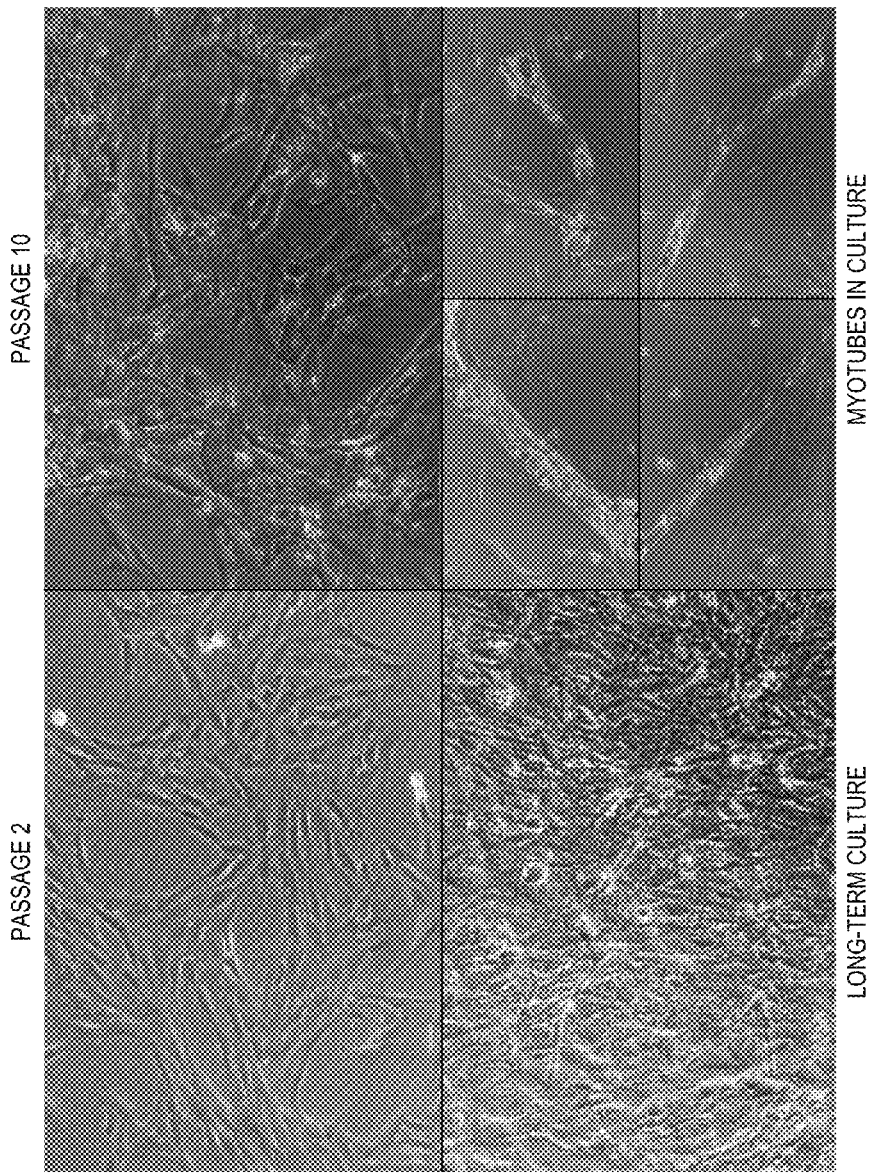
FIG. 3 shows a morphology of an established patient cardiac myocyte cell line and myotube formation according to the technique described in the various embodiments of the present invention.

Characterization of generated cardiac cell lines: (i) Cell Morphology: The cardiac myocyte cell line is homogenous in morphology and shows typical morphology of cardiac myocytes (FIG. 3). They grow attaching to each other as stripes at a lower confluency and on top of each other when grown to confluency and detach as sheets during subculturing.

(ii) Myotube formation. The cardiac myocyte cell line formed myotubes in culture (FIG. 3). Myotubes are formed by cell fusions, which is one of the functional characters of cardiac myocytes. This further support the cell line obtained is cardiac myocytes.

(iii) Growth: The cardiac myocyte cell lines continuously proliferate at least for 12 passages in vitro. The doubling time at passage 4 is 38.2 hrs.

Figure 4:
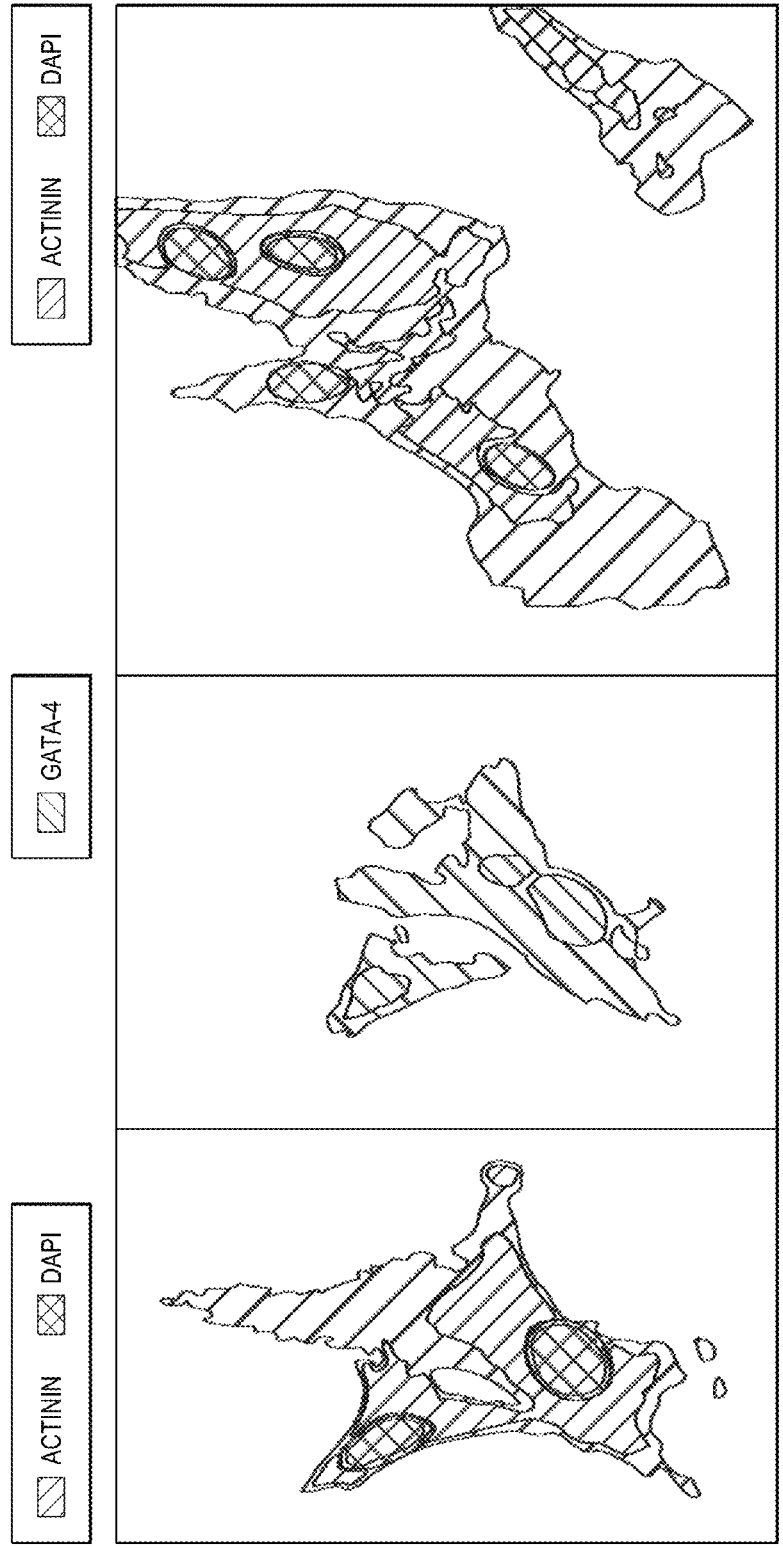
FIG. 4 shows expression of cardiac cell markers of established cardiac myocyte cell line.

(iv) Expression of cardiac myocyte cell markers: Immunostaining showed 100% of the cells express cardiomyocytes marker sarcomeric α-Actinin. About 30% are positive for cardiomyocytes-specific transcription factor GATA-4 (FIG. 4).

Authentication of the obtained cardiac myocyte cell line was done by short tandem repeat (STR) analysis to verify the cell line was originated from patient's fibroblasts (Table 1). Results showed the parental fibroblast, iPSCs and derived cardiac myocyte cell line have identical genetic markers indicating they are all originated from identical person. The analysis also confirmed that there is no inter-species contamination.

TABLE 1

Authentication for established cardiac myocyte cell line.
Marker Analysis for Human Cell Lines

| Marker Name | Patient fibroblast 1 Alleles | Expected Alleles #: NA | Patient fibroblasts derived iPSCs 2 Alleles | Expected Alleles #: NA | Established patient cardiac myocyte cell line 3 Alleles | Expected Alleles #: NA |
|---|---|---|---|---|---|---|
| Amelogenin | X, Y | NA | X, Y | NA | X, Y | NA |
| CSF1PO | 10, 11 | NA | 10, 11 | NA | 10, 11 | NA |
| D13S317 | 11 | NA | 11 | NA | 11 | NA |
| D16S539 | 11, 14 | NA | 11, 14 | NA | 11, 14 | NA |
| D5S818 | 11, 12 | NA | 11, 12 | NA | 11, 12 | NA |
| D7S820 | 9, 12 | NA | 9, 12 | NA | 9, 12 | NA |
| THO1 | 7, 9.3 | NA | 7, 9.3 | NA | 7, 9.3 | NA |
| TPOX | 8 | NA | 8 | NA | 8 | NA |
| vWA | 17, 19 | NA | 17, 19 | NA | 17, 19 | NA |

The derived cardiac cell line was further characterized for the expression of cardiac lineage marker, ion channels and calcium ($Ca^{2+}$) handling proteins. The cardiac cell line expressed ISL1 (a marker for a cardiac progenitor cell lineage, Accession No. NM_002202.2 (human), NM_021459.4 (mouse)) at a similar level of that in the beating clusters of cardiomyocytes. The cardiac cell line also showed the expression of sodium ($Na^+$), potassium ($K^+$) and $Ca^{2+}$ channels and the $Ca^{2+}$ handling proteins, Triadin and Junctin. FIG. 5 shows the ISL1 mRNA expression in derived cardiac cell line and beating clusters of cardiomyocytes (CM).

FIG. 6 shows a quantitative mRNA analysis of ion channel subunits and $Ca^{2+}$ handling proteins in derived cardiac cell line. ($Na^+$ channel: SLC8A1; $K^+$ channels: KCNH2, KCNN1 and KCNJ2; $Ca^{2+}$ channel and handling proteins: CACNA1C, SERCA2a, Triadin and Junctin). Values are normalized to 18S and represented as the percentage of those in beating clusters of cardiomyocytes (CM).

Figure 7:
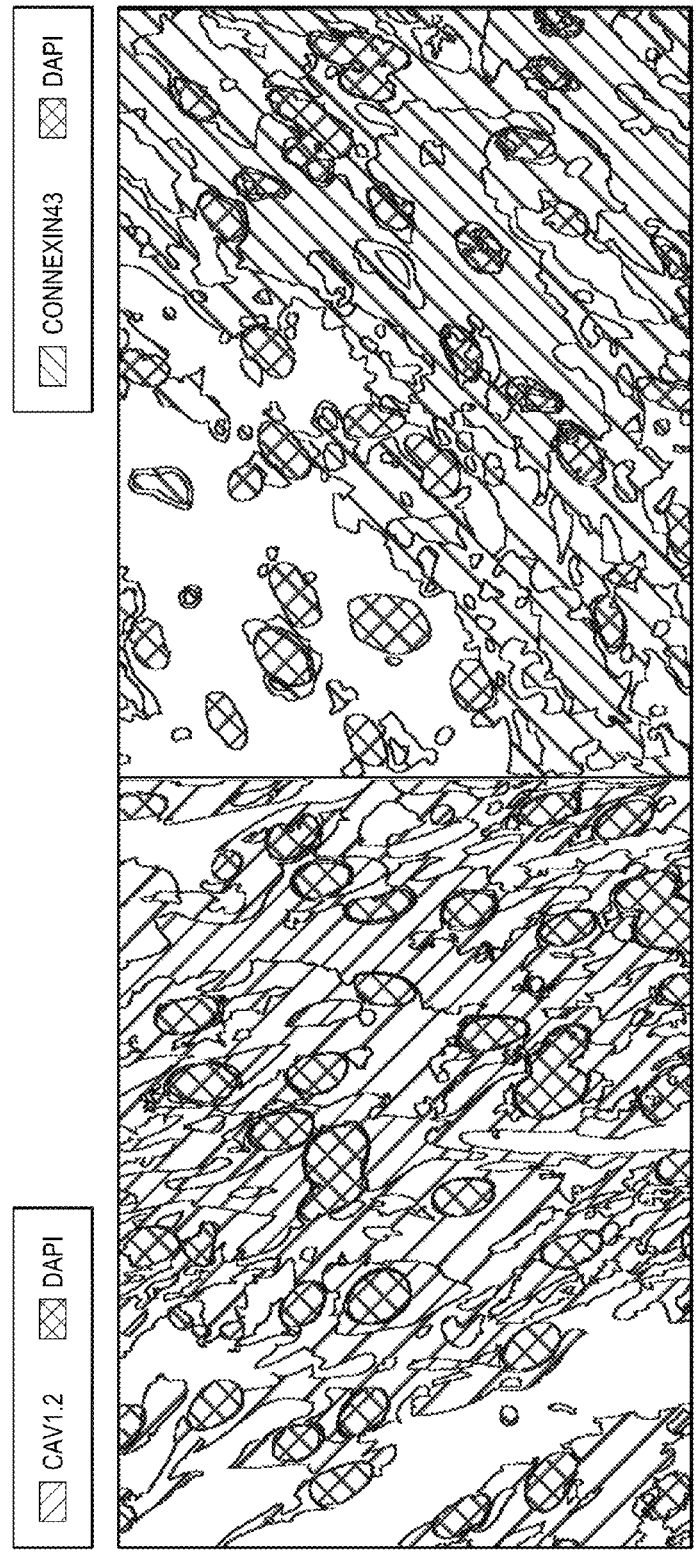
FIG. 7 shows immunostaining for L-type Ca2+ channel α-subunit (Cav1.2) and Connexin43 in derived cardiac cell line by specific antibodies.

Next, ion channel protein and gap junction protein expression was studied by immunocytochemical method. The expression of L-type $Ca^{2+}$ channel and connexin43 was confirmed in derived cardiac cell line. The expression and distribution of $Ca^{2+}$ channel and gap junction protein suggest the morphological and functional integrity of the cardiac cell line, which is important for generating electrical activity and electrical propagation, characteristic of cardiac cells. FIG. 7 shows immunostaining for L-type $Ca^{2+}$ channel α-subunit (Cav1.2) and Connexin43 in derived cardiac cell line by specific antibodies.

Figure 8:
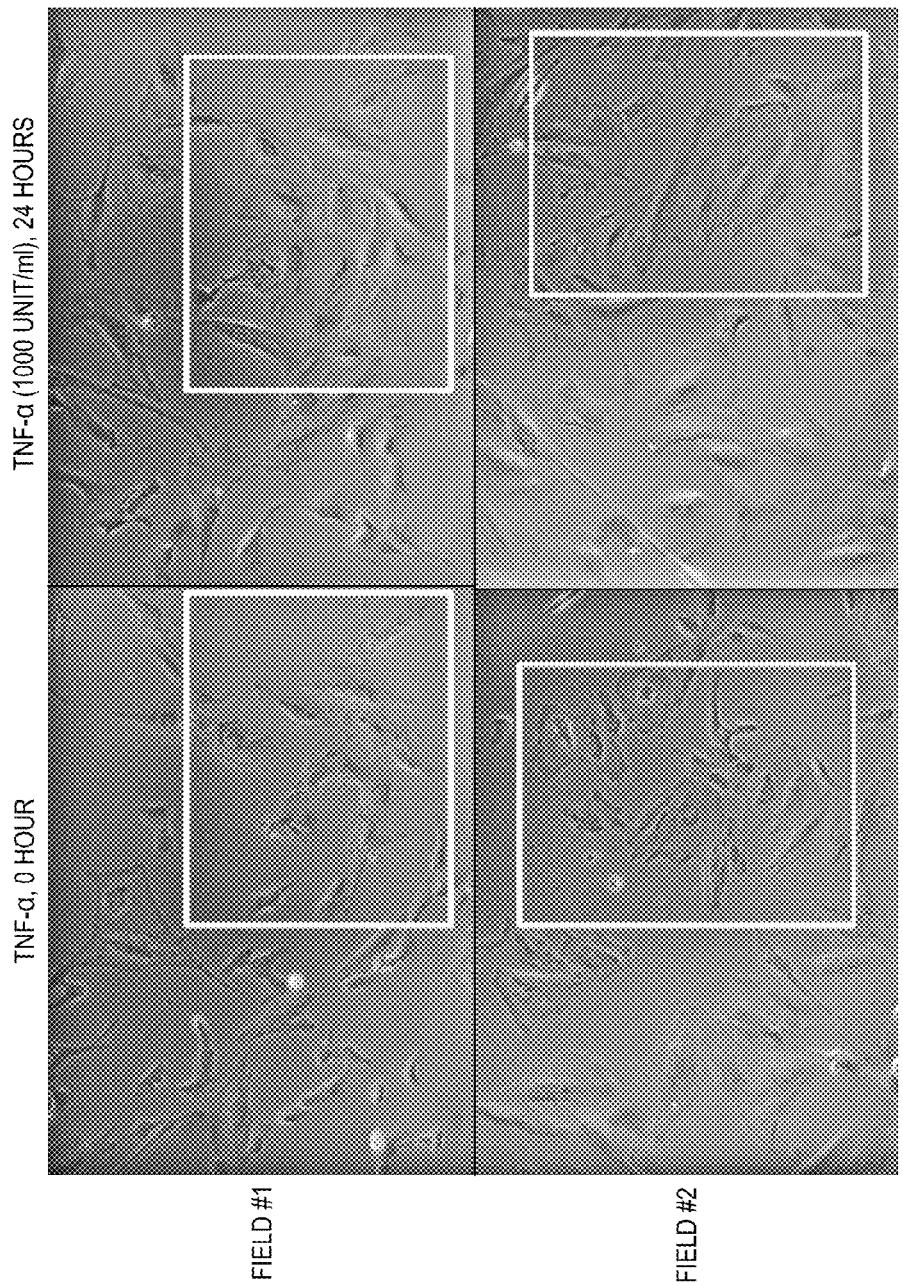
FIG. 8 shows phase-contrast images of representative two fields of derived cardiac cell line before and after (24 hrs) with TNF-α.

The effect of hypertrophy inducing drugs on derived cardiac cell line was tested. A response to cardiac toxic reagents is important in evaluating the properties of derived cardiac cell line and the future usage of the cells for testing cardiac toxic reagents as well as the mechanistic study on cardiomyopathy. Tumor necrosis factor (TNF)-α was used for the induction and compared the cell size changes at 24 hrs after drug administration. There is an increase in the sizes of treated cardiac cells. FIG. 8 shows phase-contrast images of representative two fields of derived cardiac cell line before and after (24 hrs) with TNF-α.

Figure 9:
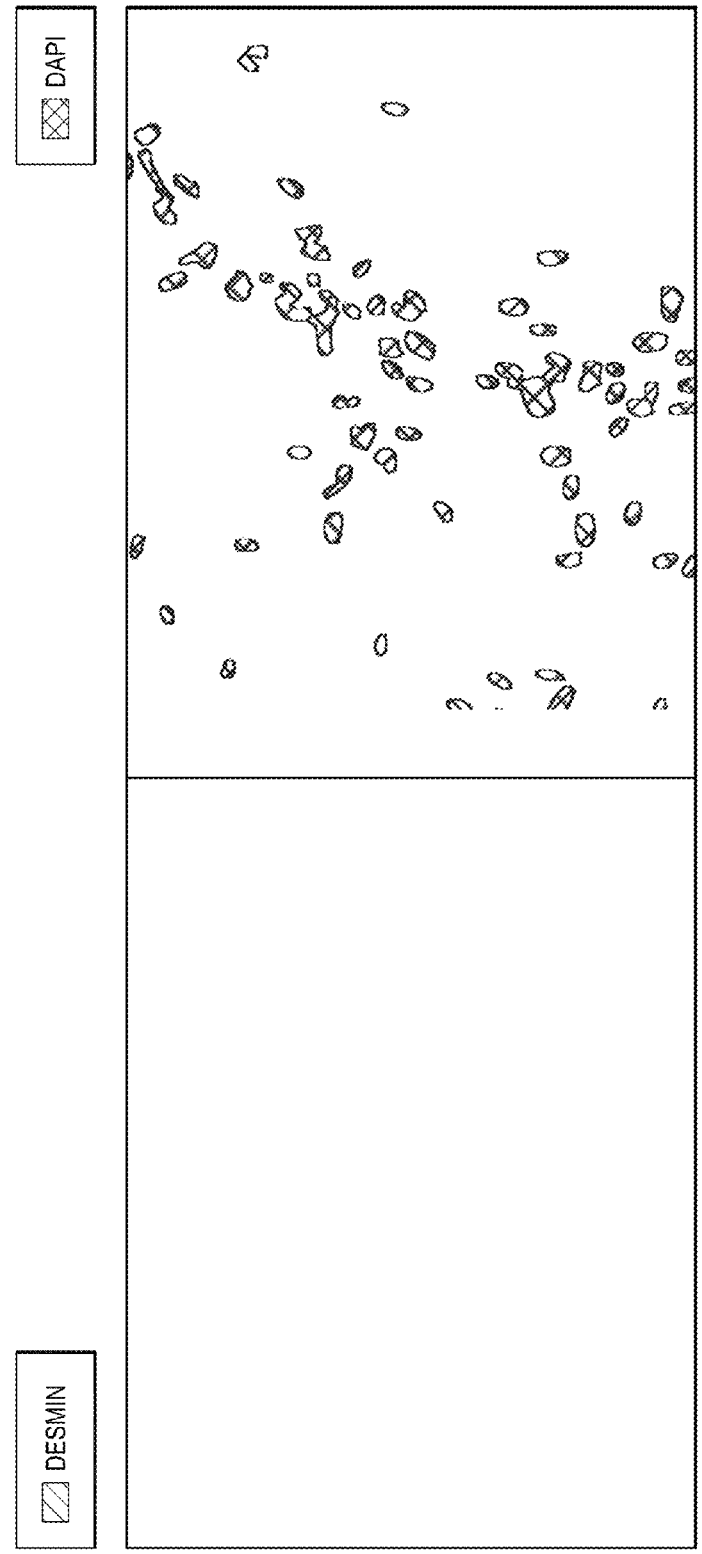
FIG. 9 shows the immunostaining of the myotubes with desmin.

Additional data on myotube formations. Immunostaining was used to stain the myotubes for desmin in order to confirm the cardiac cell identity. The myotubes were positive for desmin. FIG. 9 shows the Immunostaining of the myotubes with desmin.

The electrophysiological characterization of the derived cardiac cell line in vitro is to be studied, which is more important for considering using the cell lines for mechanistic studies of cardiac physiology and pathology. However in therapeutic studies, it is possible that transplanted cell lines can follow the intrinsic niche to further differentiate and integrate to the environment and develop proper electrophysiology of the site of integration. In vivo transplantation studies can be designed for this purpose.

It is contemplated that any embodiment discussed in this specification can be implemented with respect to any method, kit, reagent, or composition of the invention, and vice versa. Furthermore, compositions of the invention can be used to achieve methods of the invention.

It may be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it may be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

PCT Patent Application No. PCT/US2011/056329: Cardiac Induced Pluripotent Stem Cells And Methods Of Use In Repair And Regeneration Of Myocardium.
U.S. Patent Application No. 2011/097799: Cardiomyocyte Production.
U.S. Patent Application Publication No. 20050037489: Methods of Generating Human Cardiac Cells and Tissues and Uses Thereof
U.S. Patent Application Publication No. 20050054092: Process for Making Transplantable Cardiomyocytes from Human Embryonic Stem Cells.
U.S. Pat. No. 7,452,718: Direct Differentiation Method for Making Cardiomyocytes from Human Embryonic Stem Cells.
U.S. Patent Application Publication No. 20090017465: Compound Screening Using Cardiomyocytes.
U.S. Pat. No. 7,611,852: Functional Cardiomyocytes from Human Embryonic Stem Cells.
1. Xu C, et al. (2002) Characterization and enrichment of cardiomyocytes derived from human embryonic stem cells. Circ Res 91(6):501-508.
2. Lloyd-Jones D, et al. (2009) Heart disease and stroke statistics—2009 update: a report from the American Heart Association Statistics Committee and Stroke Statistics Subcommittee. Circulation. 119(3): e21-181.
3. Taylor D A, Zenovich A G. (2008) Cardiovascular cell therapy and endogenous repair. Diabetes Obes Metab. 10 Suppl 4:5-15.
4. Yazawa M, et al. (2011) Using induced pluripotent stem cells to investigate cardiac phenotypes in Timothy syndrome. Nature 471(7337):230-234.
5. Laflamme M A, et al. (2007) Cardiomyocytes derived from human embryonic stem cells in pro-survival factors enhance function of infarcted rat hearts. Nat Biotechnol 25(9):1015-1024.
6. Kehat I, et al. (2001) Human embryonic stem cells can differentiate into myocytes with structural and functional properties of cardiomyocytes. J Clin Invest 108(3):407-414.
7. Zhang J, et al. (2009) Cardiac bodies: a novel culture method for enrichment of cardiomyocytes derived from human embryonic stem cells. Functional cardiomyocytes derived from human induced pluripotent stem cells. Circ Res 104(4):e30-41.
8. Mummery C, et al. (2003) Differentiation of human embryonic stem cells to cardiomyocytes: role of coculture with visceral endoderm-like cells. Circulation 107(21):2733-2740.
9. Paige S L, et al. (2010) Endogenous Wnt/beta-catenin signaling is required for cardiac differentiation in human embryonic stem cells. PLoS One 5(6):e11134.
10. Yang L, et al. (2008) Human cardiovascular progenitor cells develop from a KDR+ embryonic-stem-cell-derived population. Nature 453(7194):524-528.

What is claimed is:

1. A method of obtaining a cardiac cell line from one or more induced pluripotent stem cells (iPSCs) comprising the steps of:
   a) culturing iPSCs in culture to form embryoid bodies;
   b) culturing the embryoid bodies so that they undergo further differentiation into beating and non-beating cardiac cell clusters;
   c) mechanically separating the beating cell clusters from the non-beating cells;
   d) culturing the non-beating cells from step c) under conditions wherein some of the cells form into beating cell clusters and some remain non-beating cells;
   e) mechanically separating the non-beating cells from the beating cell clusters formed in step d); and
   f) culturing and expanding the non-beating cells from step e) to form a cardiac cell line.

2. The method of claim 1, further comprising the step of repeating one or more steps in steps b) through e).

3. The method of claim 1, wherein the method further comprising a step of obtaining one or more iPSCs.

4. The method of claim 3, wherein the step of obtaining one or more iPSCs comprises:
   providing a primary culture comprising one or more non-pluripotent cells obtained from a mammalian subject; and
   transfecting one or more transcription factors or stem cells-associated genes into the one or more non-pluripotent cells, wherein the transfection results in the formation of the iPSCs from the non-pluripotent cells.

5. The method of claim 4, wherein the non-pluripotent cells comprise fibroblasts, blastocytes, keratocytes, aminocytes, gastric cells, neural stem cells, or any combinations thereof.

6. The method of claim 4, wherein the one or more transcription factors are selected from the group consisting of Sox2, Oct3/4, Klf4, c-Myc, Lin28, Nanog, or any combinations thereof.

7. The method of claim 3, wherein the step of obtaining one or more iPSCs comprises:
   providing a primary culture comprising one or more skin fibroblast cells obtained from a mammalian subject; and
   transfecting one or more transcription factors selected from the group consisting of Sox2, Oct3/4, Klf4, c-Myc, or any combinations thereof into the one or more skin fibroblast cells, wherein the transfection results in the formation of the iPSCs from the skin fibroblast cells.

8. The method of claim 1, wherein the iPS cells are obtaining from a mammalian subject, a human subject, a healthy subject, or a subject suffering from one or more cardiovascular diseases or metabolic disorders.

9. The method of claim 8, wherein the metabolic disorder is Fabry's disease.

10. The method of claim 1, wherein the step of culturing iPSCs comprises formation of one or more embryoid bodies, or by exposing iPSCs to factors such as BMP4 or activin A.

11. The method of claim 1, wherein the step of separating beating clusters comprises one or more mechanical methods.

12. The method of claim 1, wherein the individually separated beating cluster has been replated at least once before the culturing step d).

13. The method of claim 1, wherein the step of removing comprises one or more mechanical methods to remove the beating cluster from non-beating cells under visual inspection.

14. The method of claim 1, wherein the cardiac cell line has a purity of about 100%.

15. The method of claim 1, wherein the cardiac cell line is adapted for use in cellular/tissue transplantation, drug activity and toxicity screening studies, optimizing a therapeutic regimen, in vitro mechanistic disease models, cell-based therapies, or any combinations thereof.

16. The method of claim 1, wherein the cardiac cell line exhibits myotube formation.

17. The method of claim 1, Further comprising culturing the cardiac cell line to continuously proliferates for at least 12 passages.

18. The method of claim 1, wherein the cardiac cell line express sarcomeric α-actinin, transcription factor GATA-4, sarcomeric myosin heavy chain (MF20), cardiac troponin T, human NKx2.5 and myosin light chain 2v or any combinations thereof.

* * * * *